US009423376B2

(12) United States Patent
Hoque et al.

(10) Patent No.: US 9,423,376 B2
(45) Date of Patent: Aug. 23, 2016

(54) DIFFERENTIAL PAIR SENSING CIRCUIT STRUCTURES

(71) Applicants: Md M. Hoque, Gilbert, AZ (US);
Patrice M. Parris, Phoenix, AZ (US);
Weize Chen, Phoenix, AZ (US);
Richard J. De Souza, Chandler, AZ (US)

(72) Inventors: Md M. Hoque, Gilbert, AZ (US);
Patrice M. Parris, Phoenix, AZ (US);
Weize Chen, Phoenix, AZ (US);
Richard J. De Souza, Chandler, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 38 days.

(21) Appl. No.: 14/265,622

(22) Filed: Apr. 30, 2014

(65) Prior Publication Data
US 2015/0316503 A1 Nov. 5, 2015

(51) Int. Cl.
| | |
|---|---|
| *G01N 27/414* | (2006.01) |
| *H01L 29/78* | (2006.01) |
| *H01L 29/66* | (2006.01) |
| *H01L 29/788* | (2006.01) |
| *H01L 21/28* | (2006.01) |
| *H01L 27/115* | (2006.01) |

(52) U.S. Cl.
CPC ........... *G01N 27/4148* (2013.01); *H01L 29/66* (2013.01); *H01L 29/66409* (2013.01); *H01L 29/78* (2013.01); *H01L 29/788* (2013.01); *H01L 21/28282* (2013.01); *H01L 27/11531* (2013.01)

(58) Field of Classification Search
None
See application file for complete search history.

(56) References Cited

U.S. PATENT DOCUMENTS

| | | | |
|---|---|---|---|
| 7,535,232 B2 | 5/2009 | Barbaro et al. | |
| 7,794,584 B2 | 9/2010 | Chodavarapu et al. | |
| 7,884,398 B2 | 2/2011 | Levon et al. | |
| 2003/0224576 A1* | 12/2003 | Yamaguchi | H01L 27/0255 438/369 |
| 2005/0230271 A1* | 10/2005 | Levon | G01N 27/4148 205/789 |
| 2008/0094074 A1 | 4/2008 | Kim et al. | |
| 2010/0301398 A1* | 12/2010 | Rothberg | G01N 27/4145 257/253 |
| 2011/0299337 A1 | 12/2011 | Parris et al. | |

OTHER PUBLICATIONS

Definition of "over" from https://www.google.com/?gws_rd=ssl#q=define+over.*
N. Y. Shen et al., Charge-Based Chemical Sensors: A Neuromorphic Approach With Chemoreceptive Neuron MOS (CvMOS) Transistors, IEEE Transactions on Electron Devices, vol. 50, No. 10, Oct. 2003.
L Ravezzi et al., A CMOS ASIC for Differential Read-out of ISFET Sensors, IEEE 8th International Conference on Electronics, Circuits and Systems, vol. 3, 2001.
P. Georgiou et al., CMOS-based programmable gate ISFET, IEEE Electronics Letters, vol. 44, No. 22, Oct. 23, 2008.
H. Wong et al., A CMOS-Integrated "ISFET-Operational Amplifier" Chemical Sensor Employing Differential Sensing, IEEE Transactions on Electron Devices, vol. 36, No. 3, Mar. 1989.
V. P. Chodavarapu et al., Differential read-out architecture for CMOS ISFET microsystems, IEEE Electronics Letters, vol. 41, No. 12, Jun. 9, 2005.

(Continued)

*Primary Examiner* — Erik Kielin (57) ABSTRACT

A differential pair sensing circuit (300) includes control gates (306, 316) for separately programming a reference transistor (350) and a chemically-sensitive transistor (351) to a desired threshold voltage Vt to eliminate the mismatch between the transistors in order to increase the sensitivity and/or accuracy of the sensing circuit without increasing the circuit size.

15 Claims, 5 Drawing Sheets

(56) References Cited

OTHER PUBLICATIONS

E. Muller et al., Differential ISFET/REFET Pairs as a Reference System for Integrated ISFET-Sensor Arrays, IEEE Conference on Solid-State Sensors and Actuators, Digest of Technical Papers, TRANSDUCERS '91., Jun. 25-27, 1991.

Y. H. Ghallab et al., A Novel PH Sensor Using Differential ISFET Current Mode Read-out Circuit, IEEE Proceedings of the International Conference on MEMS, NANO and Smart Systems, (ICMENS '03), 2003.

N. Y. Shen et al., The Chemoreceptive Neuron MOS Transistors (CvMOS): A Novel Floating-Gate Device for Molecular and Chemical Sensing, IEEE 12th International Conference on Sold State Sensors, Actuators and Microsystems, Bostin, Jun. 8-12, 2003.

B. C. Jacquot et al., Time-Resolved Ion and Molecule Transport Sensing with Microfluidic Integration by Chemoreceptive Neuron MOS Transistors (CvMOS), IEEE Sensors, Oct. 20-Nov. 3, 2005.

* cited by examiner

DIFFERENTIAL PAIR SENSING CIRCUIT STRUCTURES

BACKGROUND OF THE INVENTION

1. Field of the Invention

The present invention is directed in general to integrated circuit devices and methods for manufacturing and operating same. In one aspect, the present invention relates to the manufacture and use of semiconductor devices having Ion-Sensitive Field Effect Transistors (ISFETs).

2. Description of the Related Art

Ion-Sensitive Field Effect Transistors (ISFETs) and Immunologically Sensitive Field Effect Transistors (IMFETs), hereafter collectively referred to as Chemically-Sensitive Field Effect Transistors (CSFETs), are used for sensing and measuring concentrations of ions and other molecules in fluids. When paired with a standard reference transistor to form a differential pair sensing circuit, the matching electrical characteristics (e.g., threshold voltage Vt) between the CSFET and the standard reference transistor are highly critical. However, the requirement that the CSFET gate be exposed to the fluid (either directly or through a target-sensitive membrane) can alter the threshold voltage of the CSFET, thereby creating a significant mismatch between the CSFET and the standard reference transistor which reduces the sensitivity and accuracy of the differential pair sensing circuit. These mismatch challenges remain, even as CMOS processes are used to fabricate differential pair circuits. For example, known CMOS CSFETs are unsatisfactory in a number of respects, including wide variation in the threshold voltage at a chosen set point (e.g., neutral pH) for the CMOS CSFETs, susceptibility to voltage drift of CMOS CSFETs during operation, and other deleterious effects that arise from the presence of fixed charge within the gate dielectric (and/or passivation layers) of the CMOS CSFETs, as well as process-induced charges within the polysilicon floating gate. As a result, the existing design, operation, and manufacturability of differential pair CSFET sensing integrated circuits is extremely difficult to implement at a practical level.

BRIEF DESCRIPTION OF THE DRAWINGS

The present invention may be understood, and its numerous objects, features and advantages obtained, when the following detailed description is considered in conjunction with the following drawings.

It will be appreciated that for simplicity and clarity of illustration, elements illustrated in the drawings have not necessarily been drawn to scale. For example, the dimensions of some of the elements are exaggerated relative to other elements for purposes of promoting and improving clarity and understanding. Further, where considered appropriate, reference numerals have been repeated among the drawings to represent corresponding or analogous elements.

DETAILED DESCRIPTION

A differential pair target sensing circuit and associated method of operation provide a mechanism for matching the electrical characteristics of a reference field effect transistor and chemically sensitive field effect transistor, (CSFET) by using one or more control gates that are capacitively coupled to the transistor gates, allowing the transistors to be programmed to a desired threshold voltage before, during or after fluid interaction. When fabricated within a CMOS platform, the disclosed differential pair target sensing circuit provides a highly sensitive and accurate sensing circuit with an efficient, compact, and low cost design that eliminates mismatch between the transistors. In selected embodiments, separate control gates may be used to bias both the reference transistor and the CSFET to suitable operating conditions such that the output of the circuit is maximized for any change in the target atom/molecule concentration in the fluid being measured. In other embodiments, a common control gate is capacitively coupled to the gates of both the reference transistor and the CSFET so that the transistors are simultaneously programmed to a desired operating condition to achieve maximum sensitivity and accuracy in determining a target atom/molecule concentration. In other embodiments, a control gate is capacitively coupled to the gate of the CSFET so that the CSFET can be programmed to the desired operating condition for purposes of reducing mismatch and increasing sensitivity and accurate measurement of target atom/molecule concentrations. By using capacitively coupled control gates to adjust any mismatched voltage threshold characteristics of the reference transistor and the CSFET, the sensitivity and accuracy of the differential pair target atom/molecule sensing circuit is greatly increased without significantly increasing the size of the circuit.

Figure 1:
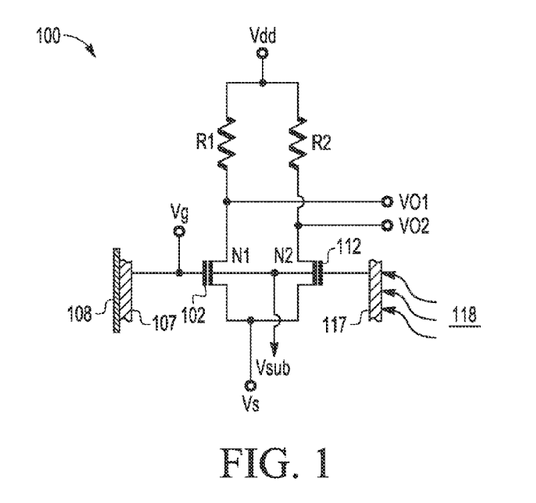
FIG. 1 shows a simplified circuit schematic diagram of a conventional differential pair CSFET sensing integrated circuit.

Turning now to FIG. 1, there is shown a simplified circuit schematic diagram of a conventional differential pair CSFET sensing integrated circuit 100 for sensing and measuring target atom/molecule concentrations in a fluid 118. The depicted sensing circuit 100 includes a series-connected first resistor R1 and standard reference FET N1 for providing a reference measurement value at output node VO1, and a series-connected second resistor R2 and chemically-sensitive FET N2 for providing a target atom/molecule measurement value at output node VO2. The measurement values VO1, VO2 may be provided as an input to an analog-to-digital converter or otherwise digitized for input to a signal processing system (not shown) for translation of the measured values to a target material property (e.g., presence, absence, amount, concentration, toxicity, etc.) measurement for the fluid 118. Coupled in parallel between a first reference voltage (e.g., Vdd) and second reference voltage (e.g., Vs), the standard and chemically-sensitive FETs N1, N2 have their gates 102, 112 connected, respectively, to a gate voltage Vg and the fluid solution 118 so that differential signal measured at the outputs VO1, VO2 quantifies the target atom/molecule concentrations in the fluid 118.

To match their threshold voltage performance, the gates 102, 112 of the standard and chemically-sensitive FETs N1, N2 are each electrically connected to identical sensing plate layers 107, 117. However, since a typical sense plate 117 for a sensitive CSFET N2 can be quite large (e.g., approximately 10,000 um$^2$ or even bigger), the requirement of a matching sense plate 107 significantly increases the size of the sensing circuit 100. In addition, the requirement of a protective layer 108 of non-reactive material on the sense plate 107 of the standard FET N1 also increases the manufacturing cost and complexity, especially if non-standard CMOS processing is required to form the protective layer 108. Other factors arising from the design, fabrication, and operation of the sensing circuit 100 can result in the standard and chemically-sensitive FETs N1, N2 having unmatched electrical characteristics which can impair the sensitivity and accuracy of the sensing circuit 100.

Figure 2:
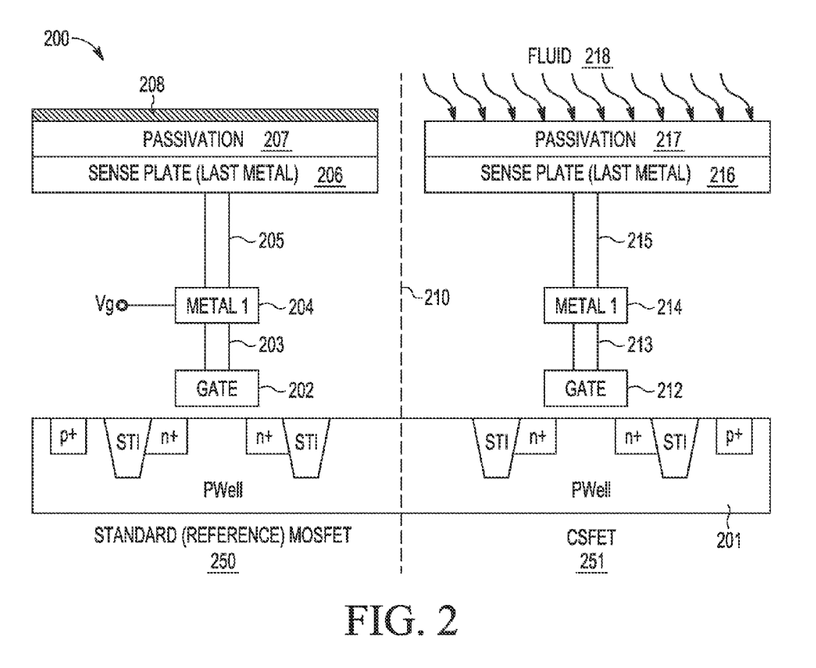
FIG. 2 shows a simplified cross-sectional view of a conventional differential pair CSFET sensing integrated circuit, such as shown in FIG. 3 shows a simplified circuit schematic diagram of a differential pair CSFET sensing integrated circuit having capacitively coupled control gates that are separately controlled in accordance with first selected embodiments of the present disclosure.

FIG. 2 shows a simplified cross-sectional view of a conventional differential pair CSFET sensing integrated circuit 200 consistent with the example sensing circuit 100 shown in FIG. 1. The depicted sensing circuit 200 includes a standard or reference MOSFET 250 and chemically-sensitive MOSFET (CSFET) 251 optionally formed in a common or shared substrate 201 and physically isolated from one another (as indicated at line 210) so that the CSFET 251 is in contact with the fluid 218 being measured. In selected embodiments, the substrate 201 is formed as up-well in a semiconductor substrate (e.g., silicon, GaAs, or another substrate material). As will be appreciated, the substrate 201 may be formed as a bulk semiconductor substrate or a semiconductor-on-insulator (SOI) type substrate in which one or more additional semiconductor layers and/or well regions are formed using epitaxial semiconductor growth and/or selective doping techniques as described more fully hereinbelow. Thus, there is no specific substrate type required. And depending on the type of device being fabricated, the substrate 201 may be implemented as a bulk semiconductor substrate, single crystalline silicon (doped or undoped), SOI substrate, or any semiconductor material including in bulk or thin-film form, for example, Si, SiC, SiGe, SiGeC, Ge, GaAs, InAs, InP, as well as other III/V or II/VI compound semiconductors or any combination thereof, alone or in combination with an epitaxial layer (e.g., p-type epi layer). However formed, the substrate 201, alone or in combination with any additional layers or regions formed therein, has an upper surface defining the uppermost extent of the substrate.

In the substrate 201, isolation regions (e.g., shallow trench isolation regions in this description) are formed to delineate and separate the MOSFET structures which include source/drain regions (e.g., regions of diffused impurities, or simply "diffusions") and the channel region formed therebetween acting in combination with a gate electrode and any electrical field generated thereby, either from the application of a gate voltage (Vg) or other electrical interaction between the gate electrode and the fluid layer being sensed. For example, the reference MOSFET 250 includes a gate electrode 202 and associated n+ source/drain regions formed in the p-well substrate 201 and isolated by STI regions from the p+ well contact region. When formed with a metal or doped poly gate layer, the gate electrode 202 may be connected through at least one via/contact layer 203 and first conductive layer 204 to receive a gate voltage (Vg). In addition, a matching sense plate layer 206 is formed in an upper conductive layer (e.g., last metal) and covered with a target atom/molecule-sensitive layer 207 (which may be the passivation layer or another layer, depending on the ion or molecule of interest), with the matching sense plate layer 206 being electrically connected to the first metal contact layer 204 by one or more via/contact layer 205. However, to protect the matching sense plate layer 206 and passivation layer 207 from the fluid 218 being measured, the passivation layer 207 is covered by protective layer 208 of non-reactive material. Though not shown, it will be appreciated that the n+ drain region of the reference MOSFET 250 is connected to an output voltage node (VO1) and across a load resistor (e,g., R1) to a first reference voltage (e.g., Vdd), While the n+ source region of the reference MOSFET 250 is connected to a second reference voltage (e.g., Vs).

In similar fashion, the CSFET 251 includes a gate electrode 212 and associated n+ source/drain regions formed in the p-well substrate 201 and isolated by STI regions from the p+ well contact region. In embodiments where the gate electrode 212 of the CSFET 251 is formed with a metal or doped poly gate layer, the gate electrode 212 may be electrically connected through at least one via/contact layer 213, first metal contact layer 214, and one or more additional via/contact layers 215 to a sense plate layer 216 formed in an upper conductive layer (e.g., last metal) and covered by a target atom/molecule-sensitive passivation layer 217 which is exposed to the fluid 218 being measured. In the illustrated embodiment, electrical communication between fluid 218 and floating gate 212 is provided by the metal sense plate 216, interconnects (e.g., vias) 213, 215, and metal structure 211 which functionally correspond to a top capacitor plate, while the substrate 201 and n+ regions formed therein form a bottom capacitor plate. Though not shown, it will be appreciated that the n+ drain region of the CSFET 251 is connected to an output voltage node (VO2) and across aloud resistor (e.g., R2) to a first reference voltage (e.g., Vdd), while the n+ source region of the CSFET 251 is connected to a second reference voltage (e.g., Vs).

During operation of the sensing circuit 200, the target atom/molecule concentration within fluid 218 results in a corresponding electrical bias of floating gate 212. This bias results in MOS behavior with respect to the n+ source/drain diffusions in the CSFET 251 to generate a signal representing the target atom/molecule concentration of fluid 218 which may be compared to a reference signal generated by the reference FET 250 in response to the gate voltage Vg. However, the presence of process-induced charge within floating gate 212 arising during manufacture or operation can significantly affect the threshold voltage of the CSFET 251, creating a mismatch between the FETs 250, 251. And in addition to the increased physical layout requirements for matching the dimensions and performance of the sense plates 206, 216, there is also additional processing required to add the protective layer 208 to the reference sense plate 206, 207 to protect it from the fluid 218 being tested. The protective layer 208 formed in the reference FET 250 not only adds to the processing complexity and cost, but can also affect the threshold voltage performance of the sensing circuit 200 by virtue of process-related changes in the fabrication of the reference FET 250. As a result, the electrical behavior of the sensing circuit 200 with respect to a given target atom/molecule concentration of fluid 218 can be difficult to predict, especially when the threshold voltages at the reference FET 250 and CSFET 251 are not matched.

The disclosed embodiments relate to a differential pair target atom/molecule sensing circuit and associated method or operation and fabrication that enables the electrical characteristics of a reference FET and CSFET in the sensing circuit to be adjusted and/or matched by using one or more control gates that are capacitively coupled to the reference FET and CSFET for programming to a desired threshold voltage. Though described with reference to MOSFET devices, it will be appreciated that the reference and chemically-sensitive transistors may be embodied with other devices, such as Metal-Oxide-Semiconductor (MOS) capacitors, metal-insulator-metal (MIM) capacitors, or the like, manufactured using standard CMOS processing techniques.

Figure 3:
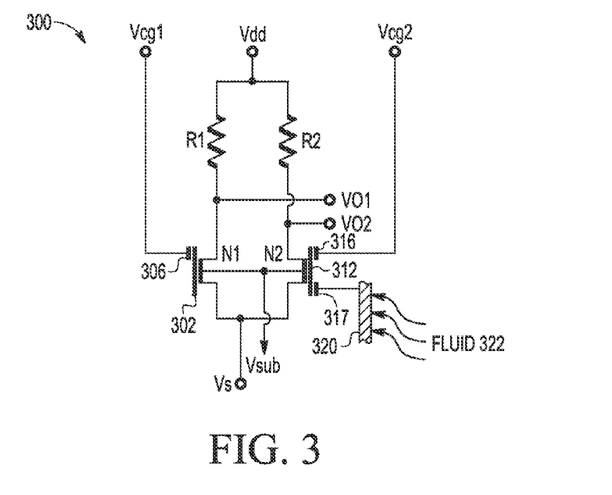

For example, FIG. 3 shows a simplified circuit schematic diagram of a differential pair CSFET sensing integrated circuit 300 having capacitively coupled control gates that are separately controlled in accordance with selected embodiments of the present disclosure. The sensing circuit 300 includes a first floating gate FET N1 with a gate electrode 302, a second floating gate FET N2 with a gate electrode 312, and load resistors R1, R2.

The floating gate FETs N1, N2 may share a common substrate voltage Vsub, and are connected with the load resistors R1, R2 in parallel between the first reference voltage (e.g., Vdd) and a second reference voltage (e.g., Vs). As a reference transistor, the first floating gate FET N1 includes a gate electrode 302 that is not connected or coupled to a target atom/molecule sensitive layer. However, a first conductive control gate or plate 306 is capacitively coupled to the gate electrode 302 to receive a first control gate voltage (Vcg1) that may be used to program the first floating gate FET N1 to a desired voltage threshold (Vt1). As a chemically-sensitive transistor, the second floating gate FET N2 includes a layer of sensing material 320 which is capacitively coupled to the gate electrode 312 via conductive plate 317, and which is in contact with the fluid 322 being measured. Sensing material layer 320 can be omitted if the material of the plate 317 is sensitive to the target atom/molecule or ion. In addition, the second floating gate FET N2 is optionally capacitively coupled to a second conductive control gate or plate 316 which receives a second control gate voltage (Vcg2) that may be used to program the second floating gate FET N2 to a desired voltage threshold (Vt2) which may be equal to or different from Vt1, depending on the nature of the mismatch between N1 and N2 and the operating range. As a result, the control gates 306, 316 may be used to program both the reference floating gate FET N1 and the chemically-sensitive floating gate FET N2 to desired threshold voltages Vt1 and Vt2 to reduce and/or eliminate the mismatch between the FETs N1, N2 in order to increase the accuracy and sensitivity of the sensing circuit 300 without increasing the size of the circuit significantly.

With the depicted sensing circuit 300, the separately controlled control gates 306, 316 allows separate programming of FETs N1, N2 which can have significant local mismatch, so that a differential signal measured at the outputs VO1, VO2 of the FETS N1, N2 can accurately quantify the target atom/molecule concentrations in the fluid 322. Though not shown, the differential signals VO1, VO2 may be provided as an input to an analog-to-digital converter (not shown) to provide digitized signals to a signal processing system (not shown) for translation of the signal to a target material property (e.g., presence, absence, amount, concentration, toxicity, etc.) measurement.

Figure 4:
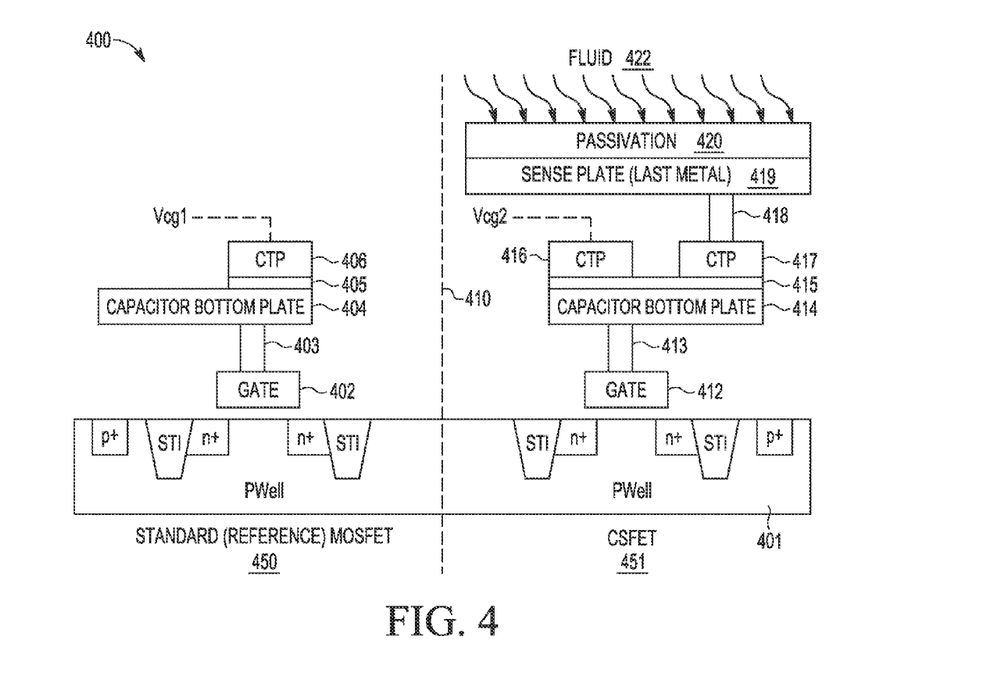
FIG. 4 shows a simplified cross-sectional view of the differential pair CSFET sensing integrated circuit shown in FIG. 3.

FIG. 4 shows a simplified cross-sectional view of a differential pair CSFET sensing integrated circuit 400 consistent with the example sensing circuit 300 shown in FIG. 3. The depicted sensing circuit 400 includes a standard or reference MOSFET 450 and CSFET 451 optionally formed in a common or shared substrate 401 and physically isolated from one another (as indicated at line 410) so that the CSFET 451 is in contact with the fluid 422 being measured. While illustrated as being formed as a p-well in a semiconductor substrate, the substrate 401 may be formed as a bulk silicon substrate, single crystalline silicon (doped or undoped), SOI substrate, or any bulk or thin-film semiconductor material including, for example, Si, SiC, SiGe, SiGeC, Ge, GaAs, InAs, InP, as well as other III/V or II/VI compound semiconductors or any combination thereof, alone or in combination with an epitaxial layer. In the substrate 401, isolation regions (e.g., shallow trench isolation as in this description) are formed to delineate and separate the standard and chemically-sensitive MOSFET structures, each of which include source/drain regions defining a channel region formed under a gate electrode. For example, the reference MOSFET 450 includes a gate electrode 402 and associated n+ source/drain regions formed in the p-well substrate 401 and isolated by STI regions from the p+ well contact region, while the chemically-sensitive MOSFET 451 includes a gate electrode 412 and associated n+ source/drain regions formed in the p-well substrate 401 and isolated by STI regions from the p+ well contact region.

At the reference MOSFET 450, the gate electrode 402 may be formed with a doped poly or metal gate layer and connected through a stack of one or more via/contact layers 403 to a capacitor bottom plate 404. In addition, a capacitor top plate (CTP) 406 is formed in an upper conductive (e.g., metal) layer and capacitively coupled through a capacitive insulating layer 405 to form a capacitor (e.g., a Metal-Insulator-Metal or MIM capacitor). With the CTP 406 connected to receive the first control gate voltage (Vcg1), the MIM capacitor may be used to program the first floating gate FET N1 to a desired voltage threshold (Vt1) by capacitively coupling the first control gate voltage across the capacitor top plate 406. Though not shown, it be appreciated that the n+ drain region of the reference MOSFET 450 is connected to an output voltage node (VO1) and across a load resistor (e.g., R1) to a first reference voltage (e.g., Vdd), while the n+ source region of the reference MOSFET 450 is connected to a second reference voltage (e.g., Vs). In addition, the p-well substrate 401 will be connected to a substrate voltage (e.g. Vsub). In embodiments where the reference MOSFET 450 does not include a sense plate layer, passivation layer, or protective layer, there will advantageously be reduced cost, processing complexity, and smaller layout requirements.

At the CSFET 451, the gate electrode 412 and associated tri-source/drain regions are isolated by STI regions in the p-well substrate 401. When formed with a metal or doped poly gate layer, the gate electrode 412 may be electrically connected through a stack of one or more via/contact layers 413 to a capacitor bottom plate 414. Over the bottom capacitor plate 414, a first capacitor top plate (CTP) 416 is formed in an upper conductive (e.g., metal) layer and capacitively coupled through a capacitive insulating layer 415 to form a capacitor (e.g., a Metal-Insulator-Metal or MIM capacitor) with the bottom capacitor plate 414. By connecting the first CTP 416 to receive the second control gate voltage (Veg2), the second floating gate FET N2 may be programmed to a desired voltage threshold (Vt2) by capacitively coupling the second control gate voltage across the first capacitor top plate 416. In addition, a second capacitor top plate (CTP) 417 may be formed in an upper metal layer and capacitively coupled through a capacitive insulating layer 415 to form a second metal-insulator-metal (MIM) capacitor with the bottom capacitor plate 414. By connecting the second CTP 417 through one or more via/contact layers 418 to a sense plate layer 419 formed in an upper metal layer (e.g., last metal) and covered by a chemically-sensitive layer 420 (which may be the passivation layer or another layer, depending on the ion or molecule of interest), the second CTP is positioned to measure the fluid 422 being tested. Layer 420 can be omitted if the material of the sense plate 419 is sensitive to the target atom/molecule or ion. In the illustrated embodiment, electrical communication between fluid 422 and floating gate 412 is provided by the metal sense plate 419, interconnects (e.g., vias) 418, second MIM capacitor 414, 415, 417, and via/contact 413. Though not shown, it will be appreciated that the n+ drain region of the CSFET 451 is connected to an output voltage node (VO2) and across a load resistor (e.g., R2) to the first reference voltage (e.g., Vdd), while the n+ source region of the CSFET 451 is connected to the second reference voltage (e.g., Vs).

In fabricating the sensing circuit 400, a single poly-multi-metal process may be employed. In selected embodiments, the gates 402, 412 may be formed by patterning a poly layer over one or more gate dielectric layers formed on the substrate 401, followed by selective implantation and/or diffusion of the source/drain and contact regions using sidewall spacers and implant masks (not shown). Interconnect layers formed over the gate electrodes 402, 412 may include one or more bottom interlayer dielectric (ILD) layers in which contact structures 403, 413 are formed in aligned contact with the gates 402, 412 and source/drain regions (not shown). In addition, a first metal layer may be formed in an upper ILD layer to define the bottom capacitor plates 404, 414, such as by using a damascene process whereby openings in an ILD layer are formed and filled with a metal (e,g., copper) that is polished to define the separate bottom capacitor plates 404, 414 in aligned contact with the contact structures 403, 413. On each bottom capacitor plate 404, 414, a capacitor dielectric 405, 415 may be formed, such as by depositing an appropriate dielectric material (e.g., oxide, nitride, etc.), alone or in combination with an etch stop layer (not shown). Subsequently, an upper metal layer may be formed in an upper ILD layer to define the top capacitor plates 406, 416, 417 as shown, such as by using a damascene process whereby openings in the upper ILD layer are formed and filled with a metal (e,g., copper) that is polished to define the separate top capacitor plates 406, 416, 417. Additional conductive interconnect layers are then formed in the upper ILD layers to connect the top capacitor plates 406, 416 to the first and second control gate voltages, respectively, and to connect the top capacitor plate 417 to the sense plate layer 419 and passivation layer 420. In this way, layout space is reduced by forming only one sense plate 419 for the differential pair and by forming the control gates 406, 416 with a metal layer that is positioned underneath the conductive sense plate layer 419. In addition, there is no need to form any protective coating on the control gates 406, 416 since they are formed in and protected by the ILD stack.

Figure 5:
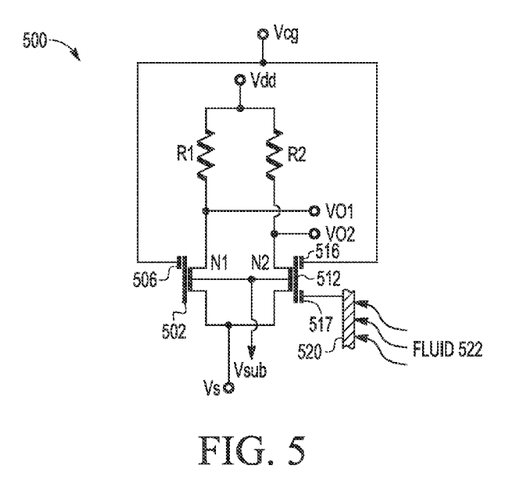
FIG. 5 shows a simplified circuit schematic diagram of a differential pair CSFET sensing integrated circuit having capacitively coupled control gates that are controlled by a shared control voltage in accordance with second selected embodiments of the present disclosure.

Turning now to FIG. 5, there is shown a simplified circuit schematic diagram of a differential pair CSFET sensing integrated circuit 500 having capacitively coupled control gates that are controlled by a shared control voltage (Vcg) in accordance with selected embodiments of the present disclosure. The sensing circuit 500 includes a first floating gate FET N1 with a gate electrode 502, a second floating gate FET N2 with a gate electrode 512, and load resistors R1, R2. The floating gate FETs N1, N2 may share a common substrate voltage Vsub, and are connected with the load resistors R1, R2 in parallel between the first reference voltage (e.g., Vdd) and a second reference voltage (e.g., Vs). As a reference transistor, the first floating gate FET N1 includes a gate electrode 502 that is not connected or coupled to a target atom/molecule sensitive layer. However, a first conductive control gate or plate 506 is capacitively coupled to the gate electrode 502 to receive a shared control gate voltage (Vcg) that may be used to program or adjust the operating conditions (e.g., voltage threshold) for the first floating gate FET N1. As a chemically-sensitive transistor, the second floating gate FET N2 includes a layer of sensing material 520 which is capacitively coupled to the gate electrode 512 via conductive plate 517, and which is in contact with the fluid 522 being measured. Layer 520 can be omitted if the material of the plate 517 is sensitive to the target atom/molecule or ion. In addition, the second floating gate FET N2 is capacitively coupled to a second conductive control gate or plate 516 which receives the shared control gate voltage (Vcg) that may be used to program or adjust the operating conditions for the second floating gate FET N2. As a result, the control gates 506, 516 may be used to simultaneously program both the reference floating gate FET N1 and the chemically-sensitive floating gate FET N2 to a desired operating condition so that a maximum sensitivity to and accuracy in determining the target atom/molecule concentration can be achieved at the sensing circuit 500 with a compact and efficient circuit. With the depicted sensing circuit 500, the FETs N1, N2 can be separately programmed but are more easily adjusted together so that a differential signal measured at the outputs VO1, VO2 of the FETs N1, N2 can accurately quantify the target atom/molecule concentrations in the fluid \.522.

Figure 6:
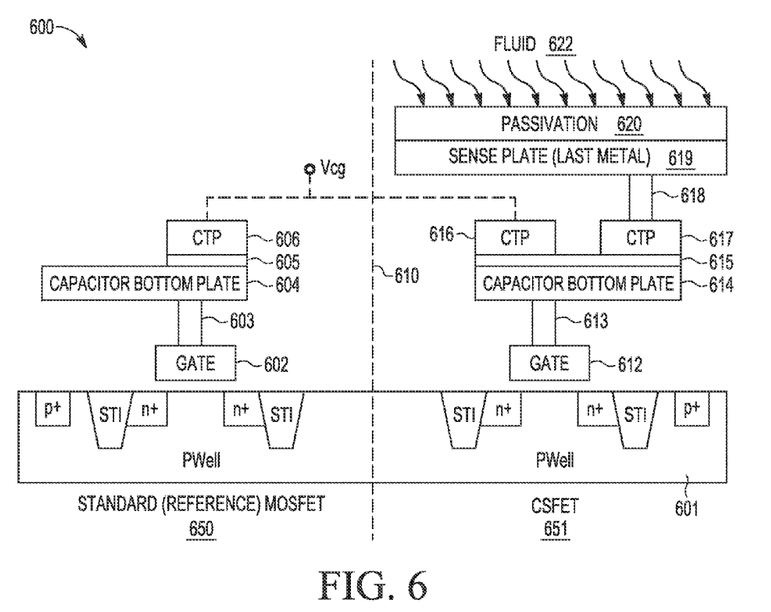
FIG. 6 shows a simplified cross-sectional view of the differential pair CSFET sensing integrated circuit shown in FIG. 5.

FIG. 6 shows a simplified cross-sectional view of a differential pair CSFET sensing integrated circuit 600 consistent with the example sensing circuit 500 shown in FIG. 5. The depicted sensing circuit 600 includes a standard or reference MOSFET 650 and CSFET 651 formed in a common or shared substrate 601 to be physically isolated from one another (as indicated at line 610) so that the CSFET 651 is in contact with the fluid 622 being measured. At the reference MOSFET 650, the gate electrode 602 may be formed with a metal or doped poly gate layer and connected through a stack of at least one via/contact layer 603 to a capacitor bottom plate 604. In addition, a capacitor top plate (CTP) 606 is formed in an upper conductive (e.g., metal) layer and capacitively coupled through a capacitive insulating layer 605 to form a first capacitor (e.g., a metal-insulator-metal or MIM capacitor). Connected to receive the shared control gate voltage (Vcg), the CTP 606 in the first MIM capacitor may be used to program the first floating gate FET N1 to a desired voltage threshold (Vt1) by capacitively coupling the shared control gate voltage (Vcg) across the capacitor top plate 606. Though not shown, it will be appreciated that the n+ drain region of the reference MOSFET 650 is connected to an output voltage node (VO1) and across a load resistor (e.g., R1) to a first reference voltage (e.g., Vdd), while the n+ source region of the reference MOSFET 650 is connected to a second reference voltage (e.g., Vs). As with other embodiments, the reference MOSFET 650 advantageously reduces cost and processing complexity and reduces the layout requirements by not including a sense plate layer, passivation layer, or protective layer.

At the CSFET 651, the gate electrode 612 and associated n+ source/drain regions are isolated by STI regions in the p-well substrate 601. In addition, the gate electrode 612 may be electrically connected through at least one via/contact layer 613 to a capacitor bottom plate 614. Over the bottom capacitor plate 614, a first capacitor top plate (CTP) 616 is formed in an upper conductive layer and capacitively coupled through a capacitive insulating layer 615 to form a second capacitor (e.g., a MIM capacitor) with the bottom capacitor plate 614. By connecting the first CTP 616 to receive the shared control gate voltage (Vcg), the second floating gate FET N2 may be programmed to a desired voltage threshold (Vt2) by capacitively coupling the shared control gate voltage (Vcg) across the first capacitor top plate 616. In addition, a second capacitor top plate (CTP) 617 may be formed in an upper conductive layer and capacitively coupled through a capacitive insulating layer 615 to form an additional capacitor (e.g., MIM capacitor) with the bottom capacitor plate 614. By connecting the second CTP 617 through one or more via/contact layers 618 to a sense plate layer 619 formed in an upper conductive layer (e.g., last metal) and covered by a target atom/molecule-sensitive passivation layer 620, the second CTP is positioned to measure the fluid 622 being tested. Layer 620 can be omitted if the material of the sense plate 619 is sensitive to the target atom/molecule or ion. Though not shown, it will be appreciated that the n+ drain region of the reference CSFET 651 is connected to an output voltage node (VO2) and across a load resistor (e.g., R2) to the first reference voltage Vdd), while the n+ source region of the CSTET 651 is connected to the second reference voltage (e.g., Vs).

In selected embodiments, the sensing circuit 600 may be fabricated with a single poly-multi-metal process. For example, after patterning the gates 602, 612 in a poly layer formed over one or more gate dielectric layers on the substrate 601, the source/drain and contact regions may be selectively implanted and/or diffused by using sidewall spacers and implant masks (not shown). Subsequently, interconnect layers are formed over the gate electrodes 602, 612 to include one or more bottom interlayer dielectric (ILD) layers in which contact structures 603, 613 are formed in aligned contact with the gates 602, 612 and source/drain regions (not shown). In addition, a first metal layer may be formed in an upper ILD layer to define the bottom capacitor plates 604, 614, such as by using a damascene process whereby openings in an ILD layer are formed and filled with a metal (e.g., copper) that is polished to define the separate bottom capacitor plates 604, 614 in aligned contact with the contact structures 603, 613. On each bottom capacitor plate 604, 614, a capacitor dielectric 605, 615 may be formed, such as by depositing an appropriate dielectric material (e.g., oxide, nitride, etc.). Subsequently, an upper metal layer may be formed in an upper ILD layer to define the top capacitor plates 606, 616, 617 as shown, such as by using a damascene process whereby openings in the upper ILD layer are formed and filled with a metal (e.g., copper) that is polished to define the separate top capacitor plates. Additional conductive interconnect layers are then formed in the upper ILD layers to connect the top capacitor plates 606, 616 to the shared control gate voltage Vcg, and to connect the top capacitor plate 617 to the sense plate layer 619 and passivation layer 620. In this way, layout space and process complexity is reduced by not forming a second sense plate and by forming the control gates 606, 616 with a metal layer that is positioned underneath the conductive sense plate layer 619 to be protected by the ILD stack.

Figure 7:
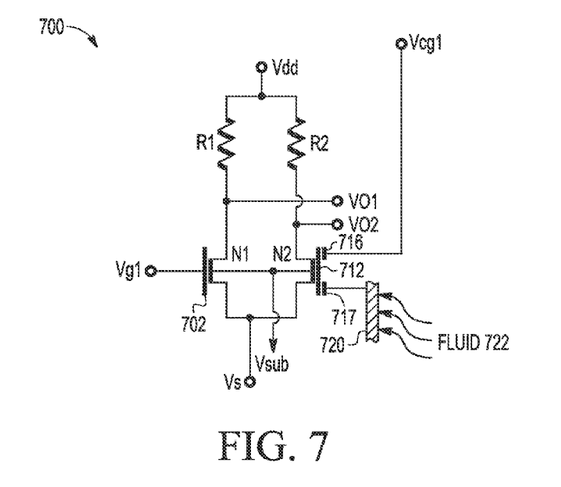
FIG. 7 shows a simplified circuit schematic diagram of a differential pair CSFET sensing integrated circuit having a control gate capacitively coupled to the CSFET gate in accordance with third selected embodiments of the present disclosure.

Turning now to FIG. 7, there is shown a simplified circuit schematic diagram of a differential pair CSFET sensing integrated circuit 700 having a control gate capacitively coupled to the CSFET gate in accordance with selected embodiments of the present disclosure. The sensing circuit 700 includes a first floating gate FET N1 with a gate electrode 702, a second floating gate FET N2 with agate electrode 712, and load resistors R1, R2. The floating gate FETs N1, N2 may share a common substrate voltage Vsub, and are connected with the load resistors R1, R2 in parallel between the first reference voltage (e.g., Vdd) and a second reference voltage (e.g., Vs). As a reference transistor, the first floating gate FET N1 includes a gate electrode 702 that is not connected or coupled to a target atom/molecule sensitive layer. Instead, the gate electrode 702 is connected to receive a first gate voltage (Vg1) that may be used to set the operating point for the sensing circuit 700. As the chemically-sensitive transistor, the second floating gate FET N2 includes a layer of sensing material 720 which is capacitively coupled to the gate electrode 712 via conductive plate 717, and which is in contact with the fluid 722 being measured. Layer 720 can be omitted if the material of the plate 717 is sensitive to the target atom/molecule or ion. In addition, the second floating gate FET N2 is capacitively coupled to a conductive control gate or plate 716 which receives the control gate voltage (Vcg) that may be used to program or adjust the operating conditions for the second floating gate FET N2. As a result, the control gate 716 may be used to program the chemically-sensitive floating gate FET N2 to a desired operating condition or voltage threshold (Vt) such that the mismatch between the standard transistor and the CSFET legs of the circuit can be minimized to obtain an increased target atom/molecule sensitivity and accuracy at the sensing circuit 700 with a compact and efficient circuit. With the depicted sensing circuit 700, the FETs N1, N2 are not separately programmed, but instead only the CSFET N2 is adjusted so that a differential signal measured at the outputs VO1, VO2 of the FETs N1, N2 can accurately quantify the target atom/molecule concentrations in the fluid 722. As will be appreciated, the sensing circuit 700 may be used for an integrated circuit fabrication process which has relatively small local mismatch, where the standard transistor is expected to be very close to the target Vt but its programmability allows its use in an even wider range of processes.

Figure 8:
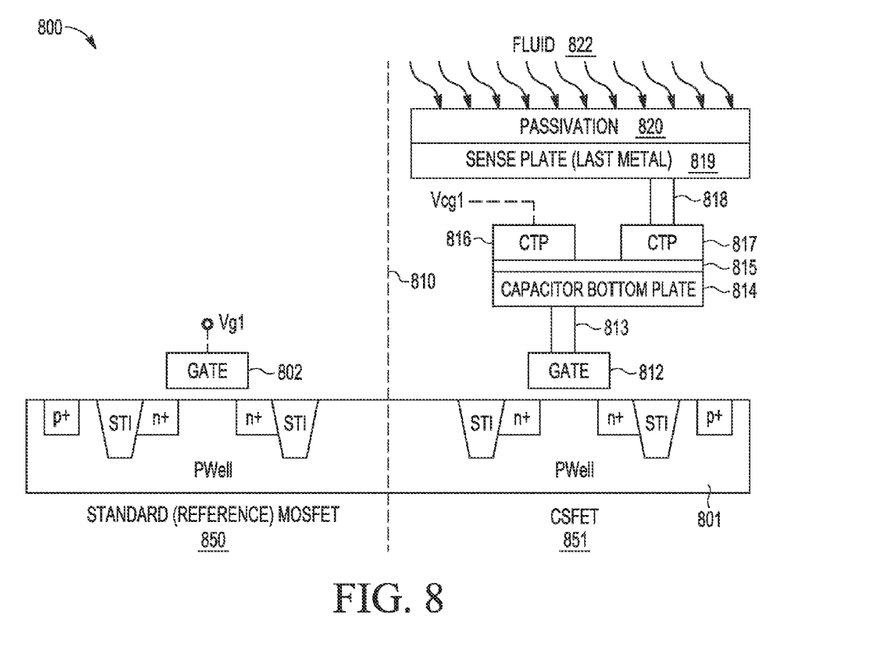
FIG. 8 shows a simplified cross-sectional view of the differential pair CSFET sensing integrated circuit shown in FIG. 7.

FIG. 8 shows a simplified cross-sectional view of a differential pair CSFET sensing integrated circuit 800 consistent with the example sensing circuit 700 shown in FIG. 7. The depicted sensing circuit 800 includes a standard or reference MOSFET 850 and CSFET 851 formed in a common or shared substrate 801 to be physically isolated from one another (as indicated at line 810) so that the CSFET 851 is in contact with the fluid 822 being measured. At the reference MOSFET 850, the gate electrode 802 may be formed with a doped poly gate layer and connected through one or more conductive interconnect layers to the first gate voltage (Vg1) without any capacitively coupling structures. Though not shown, it will be appreciated that the n+ drain region of the reference MOSFET 850 is connected to an output voltage node (VO1) and across a load resistor (e.g., R1) to a first reference voltage (e.g., Vdd), while the n+ source region of the reference MOSFET 850 is connected to a second reference voltage (e.g., Vs). As with other embodiments, the reference MOSFET 850 advantageously reduces cost and processing complexity and reduces the layout requirements by not including a sense plate layer, passivation layer, or protective layer.

At the CSFET 851, the gate electrode 812 and associated n+ source/drain regions are isolated by STI regions in the p-well substrate 801. In addition, the gate electrode 812 may be electrically connected through at least one via/contact layer 813 to a capacitor bottom plate 814. In some process technologies, the contact/via(s) connecting the gate to the capacitor bottom plate will be unnecessary since these technologies will allow the capacitor to be formed with the gate layer as its bottom plate layer. Over the bottom capacitor plate 814, a first capacitor top plate (CTP) 816 is formed in an upper conductive layer (e.g., metal) and capacitively coupled through a capacitive insulating layer 815 to form a first capacitor (e.g., MIM capacitor) with the bottom capacitor plate 814. By connecting the first CTP 816 to receive control gate voltage (Vcg), the second floating gate FET N2 may be programmed to a desired voltage threshold (Vt) by capacitively coupling the control gate voltage (Vcg) across the first capacitor top plate 816. In addition, a second capacitor top plate (CTP) 817 may be formed in an upper conductive (e.g., metal) layer and capacitively coupled through a capacitive insulating layer 815 to form a second capacitor (e.g., MIM capacitor) with the bottom capacitor plate 814. By connecting the second CTP 817 through one or more via/contact layers 818 to a sense plate layer 819 formed in an upper conductive layer (e.g., last metal) and covered by a target atom/molecule-sensitive passivation layer 820, the second CTP is positioned to measure the fluid 822 being tested. Layer 820 can be omitted if the material of the sense plate 819 is sensitive to the target atom/molecule or ion. Though not shown, it will be appreciated that the n+ drain region of the reference CSFET 851 is connected to an output voltage node (VO2) and across a load resistor (e.g., R2) to the first reference voltage (e.g., Vdd), while the n+ source region of the CSFET 851 is connected to the second reference voltage (e.g., Vs).

In selected embodiments, the sensing circuit 800 may be fabricated with a single poly-multi-metal process. For example, after patterning the gates 802, 812 in a poly layer formed over one or more gate dielectric layers on the substrate 801, the source/drain and contact regions may be selectively implanted and/or diffused by using sidewall spacers and implant masks (not shown). Subsequently, interconnect layers are formed over the gate electrodes 802, 812 to include one or more bottom interlayer dielectric (ILD) layers in which conductive contact structures (e.g., Vg1 conductor(s) and contact structures 813) are formed in aligned contact with the gates 802, 812 and source/drain regions (not shown). In addition, a first metal layer may be formed in an upper (ILD) layer to define the bottom capacitor plate 814, such as by using a damascene process whereby openings in an ILD layer are formed and filled with a metal (e.g., copper) that is polished to define the separate bottom capacitor plate 814 in aligned contact with the contact structure 813. On the bottom capacitor plate 814, a capacitor dielectric layer 815 may be formed, such as by depositing an appropriate dielectric material (e.g., oxide, nitride, etc.). Subsequently, an upper metal layer may be formed in an upper ILD layer to define the top capacitor plates 816, 817 as shown, such as by using a damascene process whereby openings in the upper ILD layer are formed and filled with a metal (e.g., copper) that is polished to define the separate top capacitor plates. Additional conductive interconnect layers are then formed in the upper ILD layers to connect the top capacitor plate 816 to the control gate voltage Vcg, and to connect the top capacitor plate 817 to the sense plate layer 819 and passivation layer 820. In this way, layout space and process complexity is reduced by not forming a second sense plate and by forming the control gate 816 with a metal layer that is positioned underneath the conductive sense plate layer 819 to be protected by the ILD stack.

Figure 9:
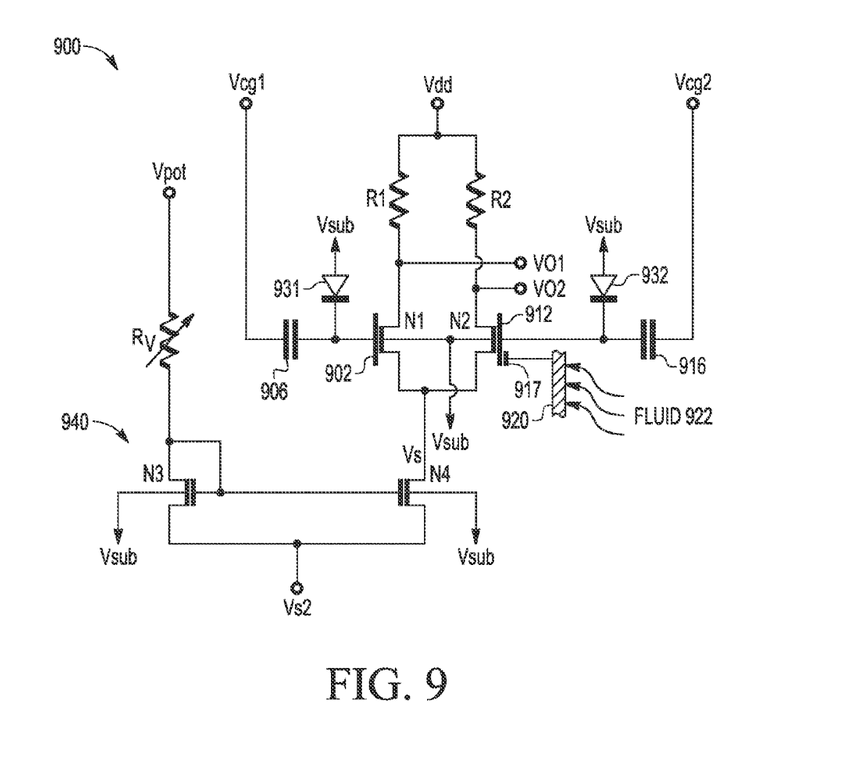
FIG. 9 shows a simplified circuit schematic diagram of a differential pair CSFET sensing integrated circuit having separate control gates capacitively coupled to the gates of a reference FET and CSFET gate in accordance with additional selected embodiments of the present disclosure.

Turning now to FIG. 9, there is shown a simplified circuit schematic diagram of a differential pair CSFET sensing integrated circuit 900 having separate, capacitively coupled control gates that may be separately controlled in accordance with selected embodiments of the present disclosure. The depicted sensing circuit 900 includes a first floating gate FET N1 with a gate electrode 902, a second floating gate FET N2 with a gate electrode 912, and load resistors R1, R2. The floating gate FETs N1, N2 are depicted as sharing a common substrate voltage ti sub and being connected with the load resistors R1, R2 in parallel between the first reference voltage (e.g., Vdd) and a second reference voltage (e.g., Vs). In addition, the first floating gate FET N1 is a reference transistor that includes a gate electrode 902 that is not connected or coupled to a target atom/molecule sensitive layer, while the second floating gate FET N2 is a chemically-sensitive transistor that includes a gate electrode 912 which is connected or coupled to a target atom/molecule sensitive layer 920 via conductive plate 917, and which is in contact with the fluid 922 being measured. Layer 920 can be omitted if the material of the plate 917 is sensitive to the target atom/molecule or ion. Each floating gate FET N1, N2 also includes a separate conductive control gate or plate 906, 916 that is capacitively coupled to the gate electrode 902, 912 (or a bottom capacitor plate electrically connected thereto) to receive a respective control gate voltage Vcg1, Vcg2. In selected embodiments, the separate conductive control gates or plates 906, 916, 917 may be formed as terminals of a MIM capacitor or fringe capacitor in a single poly process to capacitively couple the control gates 906, 916 and the sense plate 917 to the floating gates 902, 912 of the floating gate FETs N1, N2. As a result, the control gates 906, 916 may be used to separately program the reference floating gate FIT N1 and the chemically-sensitive floating gate FET N2 to a desired threshold voltage Vt to reduce and/or eliminate the mismatch between the FETs N1, N2 in order to increase the sensitivity and accuracy of the sensing circuit 900 with an efficient and compact circuit.

In accordance with any of the embodiments disclosed herein, it will be appreciated that additional circuitry may be included to enhance or modify the sensing performance. For example, gate protection diodes 931, 932 connected respectively to the gate electrodes 902, 912 (e.g., at the bottom plates of the capacitors) can improve the matching between the standard transistor and the CSFET and also provide electrostatic protection for the sensing circuit 900. In addition or in the alternative, each of the passive load resistors R1, R2 may be replaced with active transistor loads. If desired, a current mirror circuit 940 may also be included to modulate the differential gain and thereby increase the sensitivity and accuracy of the sensing circuit 900. In selected example embodiments, the current mirror circuit 940 may include a potentiometer voltage Vpot connected through a variable resistor Rv to the drain of a third NMOS transistor N3. With the source of the third NMOS transistor N3 connected to a reference voltage (e.g., Vs2), drain and gate of the third NMOS transistor N3 connected to the gate of a fourth NMOS transistor N4, the fourth NMOS transistor may be source-drain connected to control the current flow and reference voltage (e.g., Vs) at the shared source node of transistors N1, N2. In yet other embodiments, the potentiometer can be replaced by an integrated active transistor to control the bias current. By providing the sensing circuit 900 with separately controlled control gates 906, 916, the FETs N1, N2 which might have significant local mismatch may be separately programmed so that a differential signal measured at the outputs VO1, VO2 of the FETs N1, N2 can accurately quantify the target atom/molecule concentrations in the fluid 922. Though not shown, the differential signals VO1, VO2 may be provided as an input to an analog-to-digital converter (not shown) to provide digitized signals to a signal processing system (not shown) for translation of the signal to a target material property (e.g., presence, absence, amount, concentration, toxicity, etc.) measurement.

With the disclosed differential pair CSFET sensing integrated circuit 900, the control gates 906, 916 can be used to bias both the standard transistor N1 and the CSFET N2 to suitable operating conditions such that the differential output of the sensing circuit 900 is maximum for any change in the target atom/molecule concentration in the fluid 922 being measured, thereby increasing the sensitivity and accuracy of the differential pair target atom/molecule sensing circuit 900 without any significant increase in the circuit size. And in contrast to other double poly control gate solutions which require gate programming or erase operations and can only be fabricated in multiple poly layer processes, the disclosed sensing circuit 900 may be fabricated with a single poly process by forming the upper capacitor plates with conductive metal layers (e.g., a MIM or fringe capacitor) which are used to capacitively couple one or more programming voltages to the floating gates of the reference and/or chemically-sensitive FETs N1, N2 to minimize their Vt mismatch for higher sensitivity and accuracy. In addition, selected embodiments of the present disclosure eliminate the requirement of forming any sensitive coating layer on a floating gate, thereby significantly reducing or eliminating the risk of potential damage from application of a high voltage on the control gate (e.g., during program/erase). This follows from the placement of the sense plate layer as the top plate of the capacitor, thereby protecting the underlying floating gate electrodes.

By now it should be appreciated that there is provided herein a differential pair target atom/molecule sensing circuit. The sensing circuit includes a reference field effect transistor and a chemically-sensitive field effect transistor (CSFET). In selected embodiments, the reference field effect transistor is source-drain connected between a first load resistor and a first reference voltage, and the CSFET includes a floating gate electrode and is source-drain is connected between a second load resistor and the first reference voltage. The sensing circuit also includes a control gate electrode that is capacitively coupled to the CSFET and configured to apply a first control gate voltage to program or otherwise adjust the CSFET to a desired threshold voltage to control (e.g., increase) sensitivity and/or accuracy of the differential pair target atom/molecule sensing circuit. In selected embodiments, the CSFET includes a sensing plate electrode that is capacitively coupled to the floating gate electrode, where the floating gate electrode is formed with a first polysilicon or metal layer, the control gate electrode is formed in a second polysilicon or metal layer, and the sensing plate electrode is formed with a third polysilicon or metal layer that is located above the second polysilicon or metal layer. In other embodiments, the sensing circuit includes a second control gate electrode that is capacitively coupled to the reference field effect transistor to apply a second control gate voltage to program or otherwise adjust threshold voltage for the reference field effect transistor to control sensitivity and/or accuracy of the differential pair target atom/molecule sensing circuit. In such embodiments, the first and second control gate voltages may be applied to program or adjust the threshold voltages for the reference field effect transistor and CSFET to substantially eliminate threshold voltage mismatch between the reference field effect transistor and CSFET and/or to substantially eliminate resistance mismatch in the differential pair sensing circuit, such as resistor mismatch between the series resistors of the reference field effect transistor and the CSFETs. For example, the first control gate voltage is different from the second control gate voltage in some embodiments, and is the same shared control gate voltage in other embodiments. In the differential pair target atom/molecule sensing circuit, a current mirror circuit may be coupled to a shared source node of the reference field effect transistor and the CSFET and/or first and second gate protection diodes may be connected, respectively, to the gate of the reference field effect transistor and the gate of the CSFET.

In another form, there is provided a method of forming a chemically-sensitive field effect transistor (CSFET) circuit. In the disclosed methodology, a substrate is provided. Over the substrate, a CSFET gate electrode and a reference field effect transistor gate electrode are formed. In addition, a first capacitor bottom plate layer is formed over and in direct electrical connection with the CSFET gate electrode. Over the first capacitor bottom plate layer, a first control gate electrode is formed that is capacitively coupled to the CSFET gate electrode. For example, the first control gate electrode may be formed with a patterned conductive layer formed on a dielectric layer that is formed on the first capacitor bottom plate layer. And over first control gate electrode, a sense plate layer is formed that is capacitively coupled to the first capacitor bottom plate layer and otherwise electrically isolated from the first control gate electrode. In selected embodiments, the CSFET gate electrode is formed with a first polysilicon or metal layer, the first control gate electrode is formed with a second polysilicon or metal interconnect layer, and the sense plate layer is formed with a third polysilicon or metal layer that is located above the first and second polysilicon or metal layers. Finally, there is formed one or more additional first conductors for supplying the first control gate electrode with a first bias voltage to program a desired threshold voltage for the CSFET formed with the CSFET gate electrode. In addition, the method may include forming a second capacitor bottom plate layer over and in direct electrical connection with the reference field effect transistor gate electrode; forming a second control gate electrode over the second capacitor bottom plate layer that is capacitively coupled to the reference field effect transistor gate electrode; and forming one or more additional second conductors for supplying the second control gate electrode with a second bias voltage to program a desired threshold voltage for a reference field effect transistor formed with the reference field effect transistor gate electrode. In some embodiments, the first and second bias voltages are different from one another, and other embodiments, the first and second bias voltages are the same voltage. In addition, the reference field effect transistor gate electrode may be formed with a polysilicon layer and the second control gate electrode may be formed with a first metal interconnect layer.

In yet another form, there is provided a differential pair target atom/molecule sensing device for determining the presence or concentration of one or more target substances in a medium. The disclosed device may include a semiconductor substrate in which is integrated a first field effect transistor and a second field effect transistor having a floating gate electrode. In addition, a capacitor bottom plate conductor may be formed over the floating gate electrode and directly electrically connected to the floating gate electrode. First and second capacitor top plate conductors may also be formed over the capacitor bottom plate conductor and capacitively coupled across a dielectric layer to the capacitor bottom plate conductor. Over the first and second capacitor top plate conductors, a sense plate layer may be formed that is directly electrically connected to the second capacitor top plate conductor, where the sense plate layer is accessible to the medium being measured and able to retain an electrical charge from the medium. Finally, one or more conductors may be formed for supplying a first control gate voltage to the first capacitor top plate conductor to program the second field effect transistor to a desired threshold voltage to adjust or increase sensitivity and/or accuracy of the differential pair target atom/molecule sensing device formed from the first and second field effect transistors. In selected embodiments, the differential pair target atom/molecule sensing device may also include an additional capacitor bottom plate conductor formed over the first field effect transistor and directly electrically connected to a gate electrode of the first field effect transistor. Over the additional capacitor bottom plate conductor, an additional top plate conductor may be formed that is capacitively coupled across a dielectric layer to the additional capacitor bottom plate conductor. Finally, one or more conductors may be formed for supplying a second control gate voltage to the additional capacitor top plate conductor to program the first field effect transistor to a desired threshold voltage to adjust or increase sensitivity and/or accuracy of the differential pair target atom/molecule sensing device.

Various illustrative embodiments the present invention have been described in detail with reference to the accompanying figures. While various details are set forth in the foregoing description, it will be appreciated that the present invention may be practiced without these specific details, and that numerous implementation-specific decisions may be made to the invention described herein to achieve the device designer's specific goals, such as compliance with process technology or design-related constraints, which will vary from one implementation to another. While such a development effort might be complex and time-consuming, it would nevertheless be a routine undertaking for those of ordinary skill in the art having the benefit of this disclosure. For example, selected aspects are depicted with reference to simplified cross sectional drawings of a semiconductor device without including every device feature or geometry in order to avoid limiting or obscuring the present invention. In addition, selected, selected aspects are shown in simplified schematic diagram form, rather than in detail, in order to avoid limiting or obscuring the present invention. And while the figures depict versions of the circuit which use n-type MOSFETs, one skilled in the art will appreciate that the equivalent versions of this circuit using p-type transistors and p-type MOSFETs for one of the reference transistor and CSFET and n-type MOSFETs for the other are also effectively described. Such descriptions and representations are used by those skilled in the art to describe and convey the substance of their work to others skilled in the art. Although the described embodiments disclosed herein are directed to methods and systems for differential pair CSFET sensing circuits, the present invention is not necessarily limited to the example embodiments illustrate herein, and various embodiments of a differential pair CSFET structure and methodology disclosed herein may be implemented with other circuit components. For example, the logic states, voltage levels, and device types (e.g., NMOS or PHOS transistors) can be changed or reversed. Thus, the particular embodiments disclosed above are illustrative only and should not be taken as limitations upon the present invention, as the invention may be modified and practiced in different but equivalent manners apparent to those skilled in the art having the benefit of the teachings herein. Accordingly, the foregoing description is not intended to limit the invention to the particular form set forth, but on the contrary, is intended to cover such alternatives, modifications and equivalents as may be included within the spirit and scope of the invention as defined by the appended claims so that those skilled in the art should understand that they can make various changes, substitutions and alterations without departing from the spirit and scope of the invention in its broadest form.

The preceding detailed description is merely illustrative in nature and is not intended to limit the embodiments of the subject matter or the application and uses of such embodiments. In addition and unless expressly stated otherwise, references herein to elements or nodes or features being "connected" together means that one element is directly joined to (or directly communicates with) another element, and not necessarily mechanically connected. Likewise, unless expressly stated otherwise, "coupled" means that one element is directly or indirectly joined to (or directly or indirectly communicates with) another element, and not necessarily mechanically connected. Thus, the circuit schematics shown in the figures may depict example arrangements of elements, but additional intervening elements, devices, features, or components may be present in an embodiment of the depicted subject matter. Furthermore, the connecting lines shown in the various figures contained herein are intended to represent exemplary functional relationships and/or physical couplings between the various elements. For the sake of brevity, conventional techniques related to semiconductor processing, CMOS devices, MOSFETs, target atom/molecule-sensitive devices, and other functional aspects of the systems (and the individual operating components of the systems) are not be described in detail herein. Thus, it will be appreciated that various embodiments described above may be produced using any desired semiconductor processing techniques, such as CMOS fabrication techniques. Further, a variety of semiconductor and conductor materials may be used, i.e., traditional metals (aluminum, copper, gold, etc.), polysilicon, silicon dioxide, silicon nitride, silicon, and the like.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A differential pair sensing circuit comprising:
   a reference field effect transistor comprising a gate electrode coupled to a first voltage; and
   a chemically-sensitive field effect transistor (CSFET) comprising a floating gate electrode, a control gate electrode connected to receive a first control gate voltage and capacitively coupled to the floating gate electrode, and a sensing plate electrode capacitively coupled to the floating gate electrode;
   where the first voltage and first control gate voltage are separate voltages and where the first control gate voltage adjusts a threshold voltage for the CSFET to control sensitivity or accuracy of the differential pair sensing circuit.

2. The differential pair sensing circuit of claim 1, where the reference field effect transistor is source-drain connected between a first load resistor and a first reference voltage, and where the CSFET is source-drain connected between a second load resistor and the first reference voltage.

3. The differential pair sensing circuit of claim 1, where the floating gate electrode is formed with a polysilicon or a metal layer, the control gate electrode is formed with a second polysilicon or metal layer, and the sensing plate electrode is formed with a third polysilicon or metal layer that is located above the second polysilicon or metal layer.

4. The differential pair sensing circuit of claim 1, comprising a second control gate electrode capacitively coupled to the gate electrode of the reference field effect transistor to apply the first voltage as a second control gate voltage to adjust a threshold voltage for the reference field effect transistor to control sensitivity or accuracy of the differential pair sensing circuit.

5. The differential pair sensing circuit of claim 4, where the first and second control gate voltages are separate voltages that are connected, respectively, to the control gate electrode and second control gate electrode to adjust the threshold voltages for the reference field effect transistor and CSFET to substantially eliminate threshold voltage mismatch between the reference field effect transistor and CSFET.

6. The differential pair sensing circuit of claim 4, where the first and second control gate voltages are separate voltages that are connected, respectively, to the control gate electrode and second control gate electrode to adjust the threshold voltages for the reference field effect transistor and CSFET to substantially eliminate threshold voltage mismatch between the reference field effect transistor and CSFET and to substantially eliminate resistance mismatch in the differential pair sensing circuit.

7. The differential pair sensing circuit of claim 1, further comprising a current mirror circuit coupled to a shared source node of the reference field effect transistor and the CSFET.

8. The differential pair sensing circuit of claim 1, further comprising first and second gate protection diodes connected, respectively, to the gate of the reference field effect transistor and the gate of the CSFET.

9. A method of forming a chemically-sensitive field effect transistor (CSFET) circuit, comprising:
    providing a substrate;
    forming a CSFET gate electrode and a reference field effect transistor gate electrode over the substrate;
    forming a first capacitor bottom plate layer over and in direct electrical connection with the CSFET gate electrode;
    forming a first control gate electrode over the first capacitor bottom plate layer that is capacitively coupled to the CSFET gate electrode;
    forming a sense plate layer over the first control gate electrode that is capacitively coupled to the first capacitor bottom plate layer and otherwise electrically isolated from the first control gate electrode;
    forming one or more additional first conductors for supplying the first control gate electrode with a first bias voltage to program a desired threshold voltage for the CSFET formed with the CSFET gate electrode; and
    forming one or more additional second conductors for coupling a second bias voltage to the reference field effect transistor gate electrode, where the first and second bias voltages are different voltages.

10. The method of claim 9, where forming the first control gate electrode comprises forming a patterned conductive layer on a dielectric layer formed on the first capacitor bottom plate layer.

11. The method of claim 9, where the CSFET gate electrode is formed with first polysilicon or metal layer, the first control gate electrode is formed with second polysilicon or metal layer, and the sense plate layer is formed with a third polysilicon or metal layer that is located above the first and second polysilicon or metal layers.

12. The method of claim 9, further comprising:
    forming a second capacitor bottom plate layer over and in direct electrical connection with the reference field effect transistor gate electrode; and
    forming a second control gate electrode over the second capacitor bottom plate layer that is capacitively coupled to the reference field effect transistor gate electrode;
    where the one or more additional second conductors couple the second bias voltage to the reference field effect transistor gate electrode by supplying the second control gate electrode with the second bias voltage to program a desired threshold voltage for a reference field effect transistor formed with the reference field effect transistor gate electrode.

13. The method of claim 12, where the reference field effect transistor gate electrode is formed with a polysilicon layer and the second control gate electrode is formed with a first metal interconnect layer.

14. A differential pair sensing device for determining the presence or concentration of one or more target substances in a medium, comprising:
    a semiconductor substrate in which is integrated a first field effect transistor and a second field effect transistor having a floating gate electrode;
    a capacitor bottom plate conductor formed over the floating gate electrode and directly electrically connected to the floating gate electrode;
    first and second capacitor top plate conductors formed over the capacitor bottom plate conductor and capacitively coupled across a dielectric layer to the capacitor bottom plate conductor;
    a sense plate layer formed directly over the first and second capacitor top plate conductors and directly electrically connected to the second capacitor top plate conductor, where the sense plate layer is accessible to the medium being measured and able to retain an electrical charge from the medium; and
    one or more conductors for supplying a first control gate voltage to the first capacitor top plate conductor to program the second field effect transistor to a desired threshold voltage to adjust sensitivity or accuracy of the differential pair sensing device formed from the first and second field effect transistors.

15. The differential pair sensing device of claim 14, further comprising:
    an additional capacitor bottom plate conductor formed over the first field effect transistor and directly electrically connected to a gate electrode of the first field effect transistor;
    an additional top plate conductor formed over the additional capacitor bottom plate conductor and capacitively coupled across a dielectric layer to the additional capacitor bottom plate conductor; and
    one or more conductors for supplying a second control gate voltage to the additional capacitor top plate conductor to program the first field effect transistor to a desired threshold voltage to adjust sensitivity and/or accuracy of the differential pair sensing device.

* * * * *